US012653710B2

(12) United States Patent
Gagne

(10) Patent No.: US 12,653,710 B2
(45) Date of Patent: Jun. 16, 2026

(54) HIP FLEXION CONTRACTURE THERAPEUTIC MEDICAL DEVICE

(71) Applicant: Arthur Gagne, Dade City, FL (US)

(72) Inventor: Arthur Gagne, Dade City, FL (US)

( * ) Notice: Subject to any disclaimer, the term of this patent is extended or adjusted under 35 U.S.C. 154(b) by 132 days.

(21) Appl. No.: 18/527,053

(22) Filed: Dec. 1, 2023

(65) Prior Publication Data

US 2024/0180733 A1     Jun. 6, 2024

Related U.S. Application Data

(60) Provisional application No. 63/429,423, filed on Dec. 1, 2022.

(51) Int. Cl.
A61F 5/01         (2006.01)
A61F 5/32         (2006.01)
(52) U.S. Cl.
CPC .............. A61F 5/0193 (2013.01); A61F 5/32 (2013.01)

(58) Field of Classification Search
CPC .......... A61F 5/0193; A61F 5/32; A61F 5/028; A61F 5/02; A61F 5/022; A61F 5/024; A61F 5/026; A61F 5/03
See application file for complete search history.

(56) References Cited

FOREIGN PATENT DOCUMENTS

JP          2022108368 A  *  7/2022

* cited by examiner

*Primary Examiner* — Ophelia A Hawthorne
(74) *Attorney, Agent, or Firm* — Cynthia S. Lamon; Lamon Patent Services

(57) ABSTRACT

A therapeutic medical device has a waistband with a ratchet buckle, a PSIS pad at a back region, two ASIS pads adjustable to impinge on a patient's ASIS points, and a socket post joined to the waistband on one side with a lever engaged in a socket of the socket post.

8 Claims, 7 Drawing Sheets

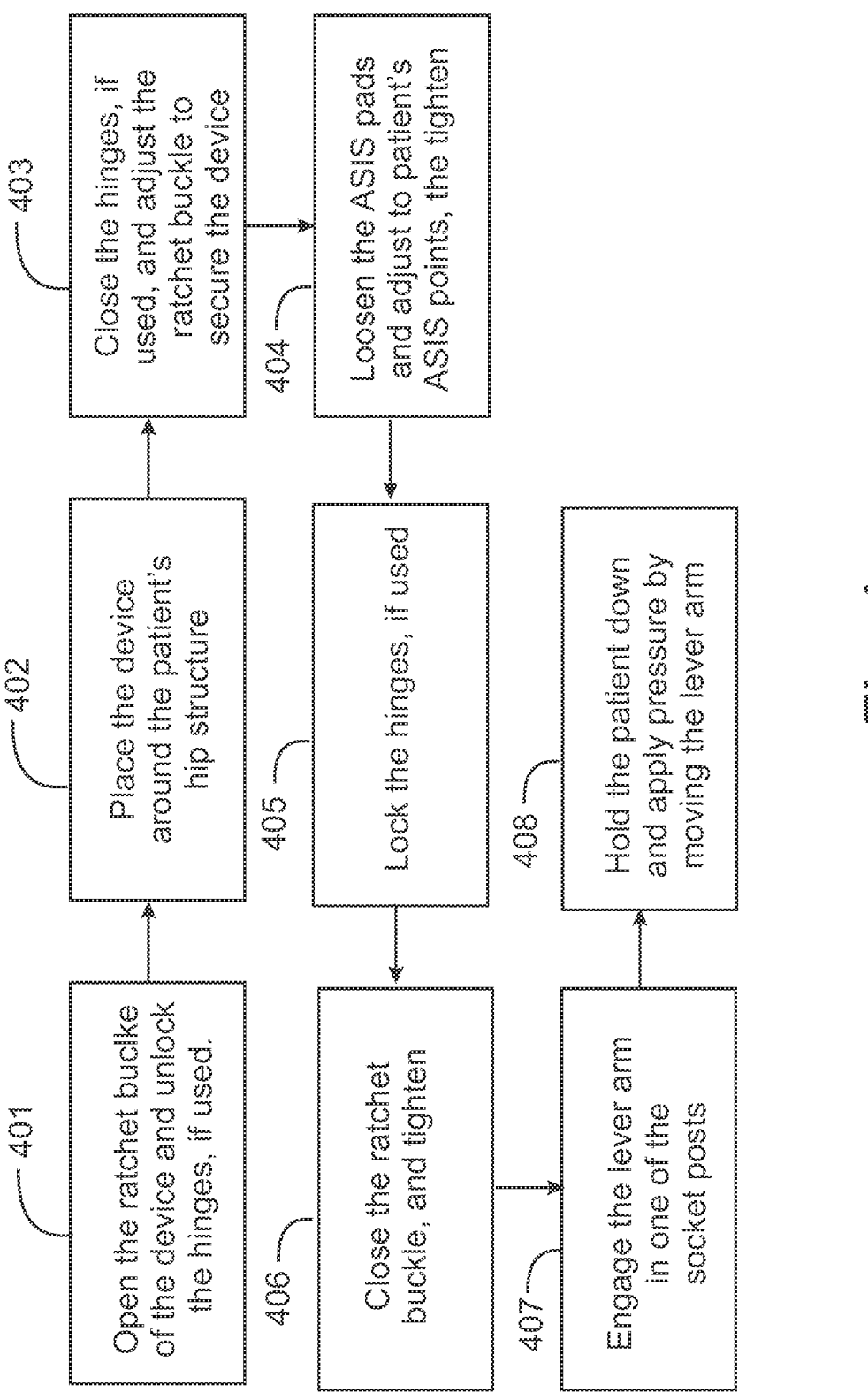

401 — Open the ratchet buckle of the device and unlock the hinges, if used.

402 — Place the device around the patient's hip structure

403 — Close the hinges, if used, and adjust the ratchet buckle to secure the device 404 — Loosen the ASIS pads and adjust to patient's ASIS points, the tighten 405 — Lock the hinges, if used 406 — Close the ratchet buckle, and tighten 407 — Engage the lever arm in one of the socket posts 408 — Hold the patient down and apply pressure by moving the lever arm

HIP FLEXION CONTRACTURE THERAPEUTIC MEDICAL DEVICE

CROSS REFERENCE TO RELATED APPLICATIONS

The present application claims priority to U.S. Provisional Patent Application 63/429,423 filed Dec. 1, 2022. All disclosure of the parent case is incorporated herein at least by reference.

BACKGROUND OF THE INVENTION

1. Field of the Invention

The present invention is in the technical field of medical devices, and pertains more particularly a therapeutic device for hip flexure.

2. Description of Related Art

Hip flexion contractures are a debilitating condition affecting mostly sedentary persons, amputees, and older adults. A primary muscle involved in hip flexion contractures is the iliopsoas muscle which in affected persons becomes stiff and shortened and is correlated with the pelvis becoming more anteriorly tilted when a patient has a hip flexion contracture. Until the present invention the primary non-invasive treatment option for Hip Flexion Contractures has been manual physical therapy. However, manual physical therapy is not optimally effective due to reliance on strength of a physical therapist applying pressure during a treatment session, and the strenuous leg maneuvers required to achieve the stretch.

What is therefore clearly needed is a therapeutic medical device that will reduce a physical therapist's applied force needed for successful treatment while increasing force application to the patient to adequately stretch the muscles, tendons, and ligaments involved in hip flexion contractures. It is believed that such a device would also decrease a physical therapist's fatigue which would potentially increase the physical therapist's ability to provide longer duration treatment.

BRIEF SUMMARY OF THE INVENTION

In one embodiment a therapeutic medical device is provided, comprising a waistband having a width and opposite ends, first and second complementary portions of a ratchet buckle joined to the opposite ends of the waistband, enabling the waistband to be opened and closed, and to be adjusted in overall circumference, a PSIS pad joined to an inside surface of the waistband at a position, with the ratchet buckle closed, opposite the ratchet buckle, a first ASIS pad joined through a slot to the inside surface of the waistband proximate a first side of the ratchet buckle, in a manner that the first ASIS pad may be adjusted along the slot and secured to the waistband by a first locking mechanism outside the waistband, a second ASIS pad joined through a slot to the inside surface of the waistband proximate a second side of the ratchet buckle, in a manner that the second ASIS pad may be adjusted along the slot and secured to the waistband by a second locking mechanism outside the waistband, a first socket post having a height less than the width of the waistband secured to the waistband through the height of the socket post at a point on the waistband about ninety degrees from the ratchet buckle, and a lever arm engaged in a socket in the socket post, the lever arm extending parallel to a plane described by the waistband.

In one embodiment the medical device further comprises a second socket post having a height less than the width of the waistband secured to the waistband through the height of the socket post at a position on the waistband directly opposite the first socket post. Also, in one embodiment each ASIS pad has a threaded post extending through the slot and a locking knob engaging the threaded post outside the waistband.

In another aspect of the invention a therapeutic medical device is provided, comprising a waistband having a width and opposite ends, a first locking hinge joined to the waistband at one of the opposite ends, and a second locking hinge joined to the waistband at the other opposite end, a first panel having a first linear slot joined to the first locking hinge and ending at a first portion of a ratchet buckle, a second panel having a second linear slot joined to the second locking hinge and ending in a second portion of the ratchet buckle, a PSIS pad joined to an inside surface of the waistband at a position, with the ratchet buckle closed, opposite the ratchet buckle, a first ASIS pad joined to the first linear slot in the first panel, and a second ASIS pad joined to the second linear slot in the second panel, a first socket post having a height less than the width of the waistband secured to the waistband through the height of the socket post at a point on the waistband about ninety degrees from the ratchet buckle, and a lever arm engaged in a socket in the socket post, the lever arm extending parallel to a plane described by the waistband.

In one embodiment the medical device further comprises a second socket post having a height less than the width of the waistband secured to the waistband through the height of the socket post at a position on the waistband directly opposite the first socket post. Also, in one embodiment each ASIS pad has a threaded post extending through the slot and a locking knob engaging the threaded post outside the waistband.

In yet another aspect of the invention a method for treating s patient for hip flexion contracture is provided, comprising placing a therapeutic medical device having a waistband having a width and opposite ends, first and second complementary portions of a ratchet buckle joined to the opposite ends of the waistband, enabling the waistband to be opened and closed, and to be adjusted in overall circumference, a PSIS pad joined to an inside surface of the waistband at a position, with the ratchet buckle closed, opposite the ratchet buckle, a first ASIS pad joined through a slot to the inside surface of the waistband proximate a first side of the ratchet buckle, in a manner that the first ASIS pad may be adjusted along the slot and secured to the waistband by a first locking mechanism outside the waistband, a second ASIS pad joined through a slot to the inside surface of the waistband proximate a second side of the ratchet buckle, in a manner that the second ASIS pad may be adjusted along the slot and secured to the waistband by a second locking mechanism outside the waistband, a first socket post having a height less than the width of the waistband secured to the waistband through the height of the socket post at a point on the waistband about ninety degrees from the ratchet buckle, and a first lever arm engaged in a socket in the socket post, the first lever arm extending parallel to a plane described by the waistband, around a hip structure of a patient, adjusting circumference of the therapeutic medical device and securing the device firmly to the patient, positioning the first ASIS pad to the patient's first ASIS point and the second ASIS pad to the patient's second ASIS point, holding the patient securely facing up against a supporting surface, and manipulating the first lever arm, rotating the patient's hip structure and stretching the patient's first iliopsoas muscle.

In one embodiment this method further comprises securing a second socket post having a height less than the width of the waistband to the waistband through the height of the second socket post at a point on the waistband opposite the first socket post, engaging a second lever arm in a socket of the second socket post, and manipulating the second lever arm, rotating the patient's hip structure and stretching the patient's second iliopsoas muscle.

BRIEF DESCRIPTION OF THE SEVERAL VIEWS OF THE DRAWINGS

FIG. 4 is a flow diagram depicting a process by which a therapist may use the device according to an embodiment of the invention.

DETAILED DESCRIPTION OF THE INVENTION

Figure 1A:
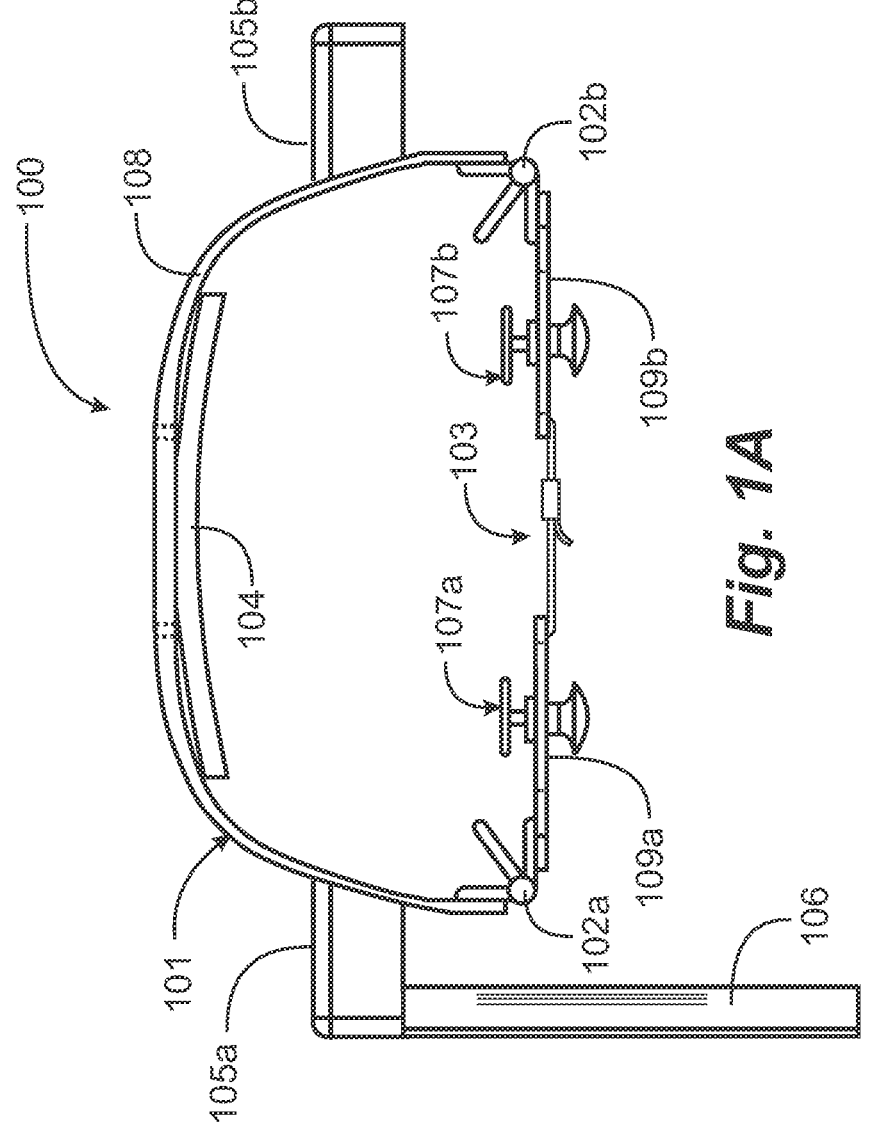
FIG. 1A is a plan view of a hip flexion medical device in an embodiment of the present invention.
Figure 1B:
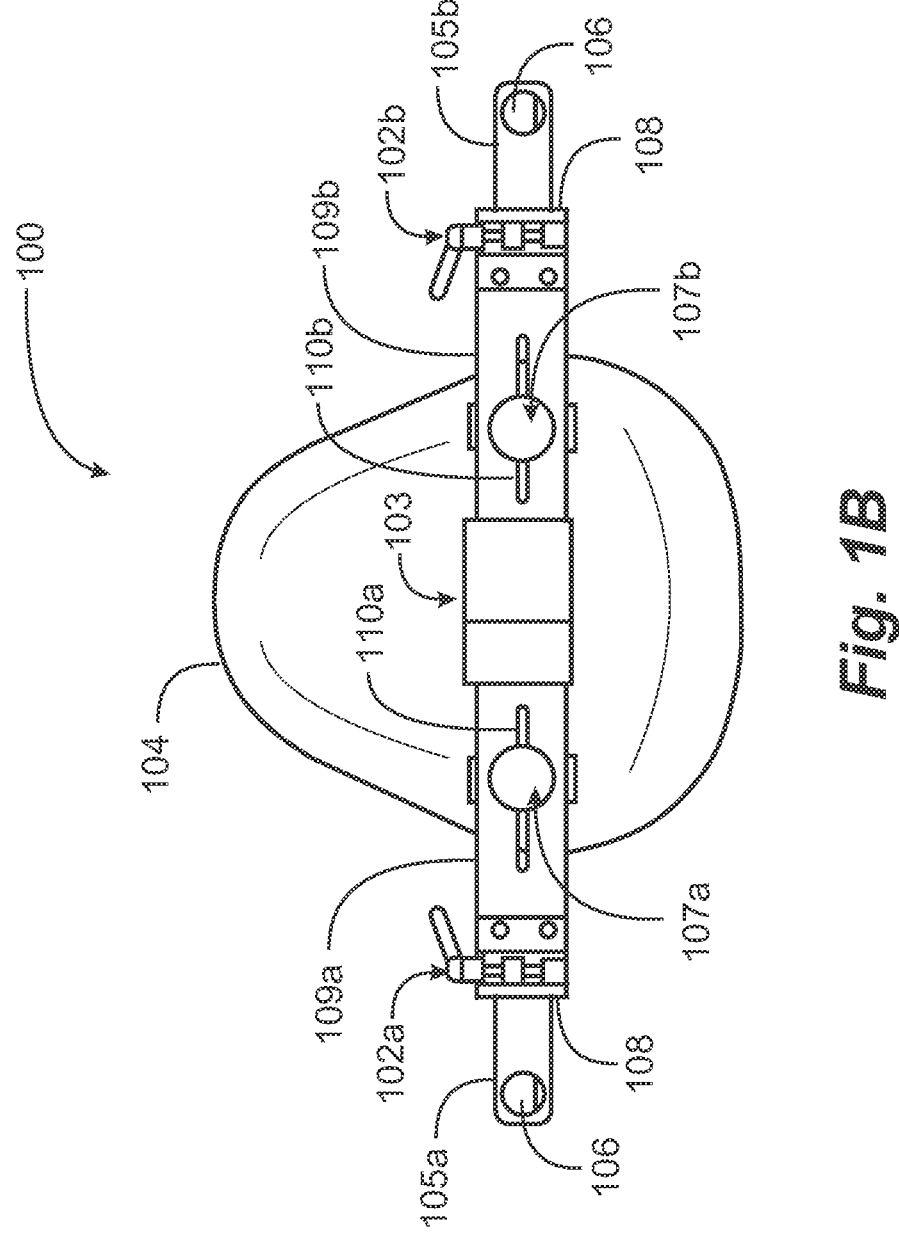
FIG. 1B is a front elevation view of the hip flexion medical device of FIG. 1A in an embodiment of the invention.
Figure 1C:
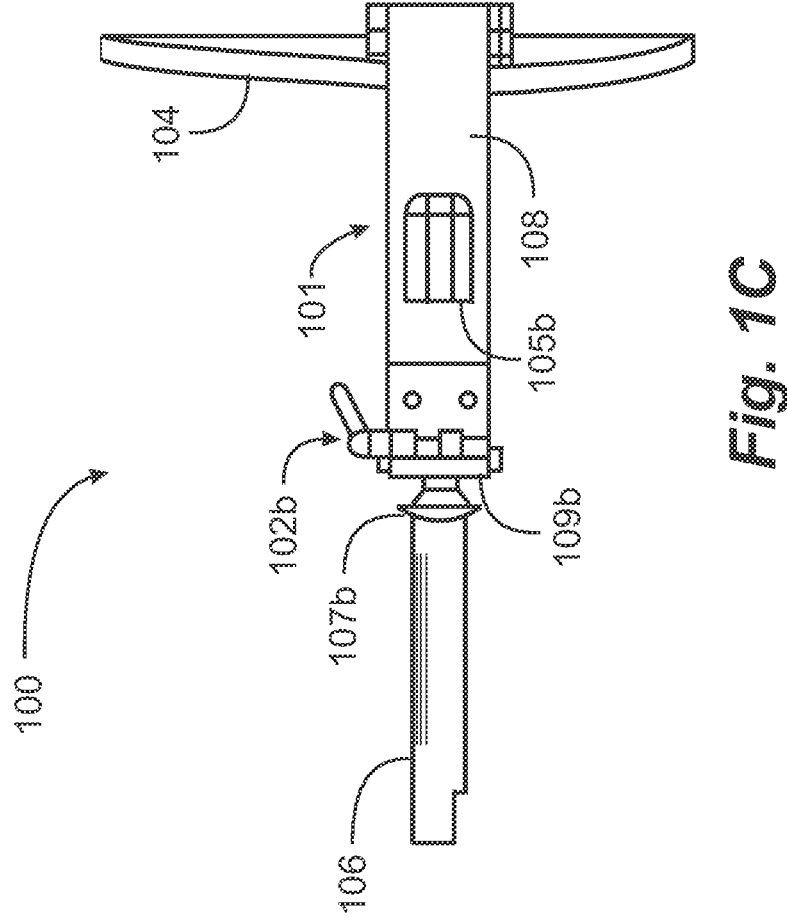
FIG. 1C is a side elevation view of the hip flexion medical device of FIGS. 1A and 1B in an embodiment of the present invention.
Figure 1D:
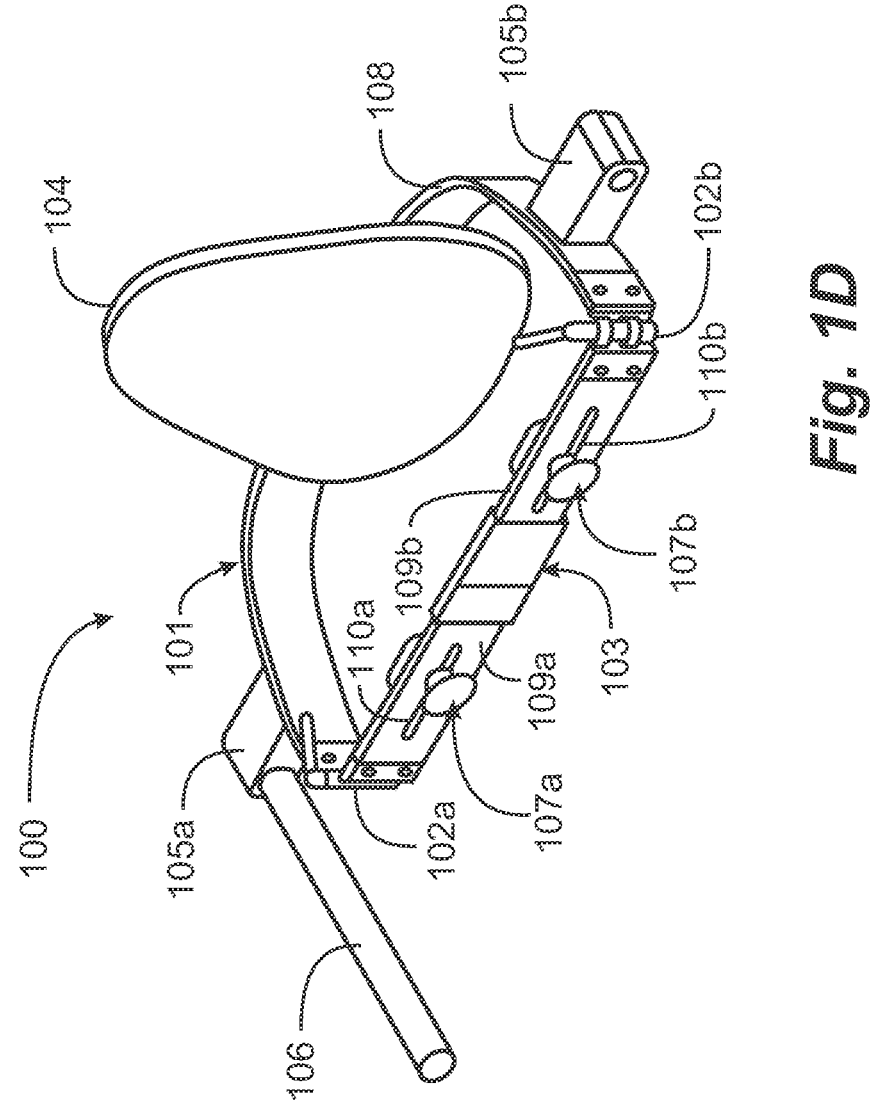
FIG. 1D is a perspective view of the hip flexion medical device of FIGS. 1A, 1B and 1C in an embodiment of the present invention.

It is well known that hip flexion contractures may be treated with manual physical therapy, but such therapy is not always effective because a physical therapist can only apply a limited amount of pressure over time to stretch the patient's anterior hip muscles. The strength and agility required to achieve the stretch are very demanding for a physical therapist.

An important objective of the invention is to provide a medical device which will enable a physical therapist or clinician to cohesively manipulate a patient's hip to treat a hip flexion contracture with less effort than may be required by manual physical therapy. Such a device should fit different upper hip anatomy sizes, create a mechanical advantage that will increase the therapist's leverage to allow for a rotational force to be translated from the device to the patient's hip, and to withstand long-term applied force by the therapist.

Design specifications for a unique device according to embodiments of the invention were developed after interviewing potential users, which are mainly physical therapists. The target market was identified as patients with hip flexion contractures and physical therapists or other authorized clinicians that can deliver manual physical therapy. A major requirement for the device is that it fits most adult sizes, therefore the device must have an adjustable circumference that fits abdominal girth sizes at the level of the Anterior Superior Iliac Spine (ASIS) of 38 to 46 inches to fit a target patient population which corresponds to overweight patients with BMI 28.8±5.15 kg/m2. Likewise, anterior pressure points must be adjustable and fit an ASIS to ASIS distance of 9.88±0.866 inches and Posterior Superior Iliac Spine (PSIS) to ASIS distances of 8.42±1.18 inches. Another major requirement for the device's functionality is that it must decrease the force that physical therapist's need to apply to rotate the hip by 4.5 times. Therefore, the distance from the pivot of the hip point to the device's force application point must be at least 12 inches. Moreover, to ensure that the device is effective in cohesively manipulating and rotating the hip, it must experience an even load distribution between its pressure points and a symmetric rotational force. Another major requirement of the device is that it must be reusable and functional for at least 8 years, therefore, the device must be sterilizable, and it must be able withstand different climates and environments, including temperatures ranging from 40 F to 100 F, as well as moisture and humidity levels of 0 to 100%. The weight of the device is another critical factor since it must be lightweight enough to be carried by the users and allow for patient ambulation, therefore the device must not weigh more than about 29 lbs. Likewise, the device must allow for patient ambulation by not restricting any lower limb joint range of motion. Furthermore, the device must withstand the forces and loads applied by the users and patients, therefore, its materials must have suitable tensile and compressive strength and its interfaces must be able to withstand an applied force of about 138 lbs. Finally, the device must be safe for the patients and users and must not cause skin irritations, allergic reactions, or skin lacerations and contusions, therefore the surfaces that come into contact with the patient or user must be non-allergenic, and the waist component must be able to be adjusted at least every 0.5 inches.

The Hip Flexure device in one embodiment of the invention is illustrated in FIGS. 1A through 1D. The device in this embodiment comprises an adjustable waistband assembly 101 that comprises a flexible strap 108 that joins to each of two locking lateral hinges 102a and 102b, one on each side of the waistband assembly, and two semi-rigid panels 109a and 109b, one joined to each lateral hinge, to adjust circumference. There are two anterior ASIS pads 107a and 107b that may be varied in position along slots in panels 109a and 109b. Each pad is fastened to the waistband in the slot by a compression knob. These pads, when properly positioned, contact the patient at ASIS points. A centrally located PSIS pad 104 contacts the patient centered on the PSIS point at the rear. In an alternative design the lateral hinges and panels 109a and 109b are not present, and the flexible strap 108 encircles the patient. This alternative makes the device more comfortable to the patient and increases the device's durability and rigidity.

In the embodiment with hinges and panels the two panels 109a and 109b are joined at ends to mating portions of a snap-in buckle 103, which may be released to remove the device, and may be engaged to secure the device around the patient. In the embodiment that used only the waistband 108 ends of the waistband join to the mating portions of buckle 103.

There are two socket posts 105a and 105b firmly attached to the waistband with interfaces for engaging a lever arm 106 to apply rotational force to the waistband and to the ASIS and PSIS pads in operation. The posts 105a and 105b each are blocks that are affixed to the waistband along a surface of the block, and each block has a socket in the direction of the plane of the waistband for inserting lever arm 106.

Figure 2:
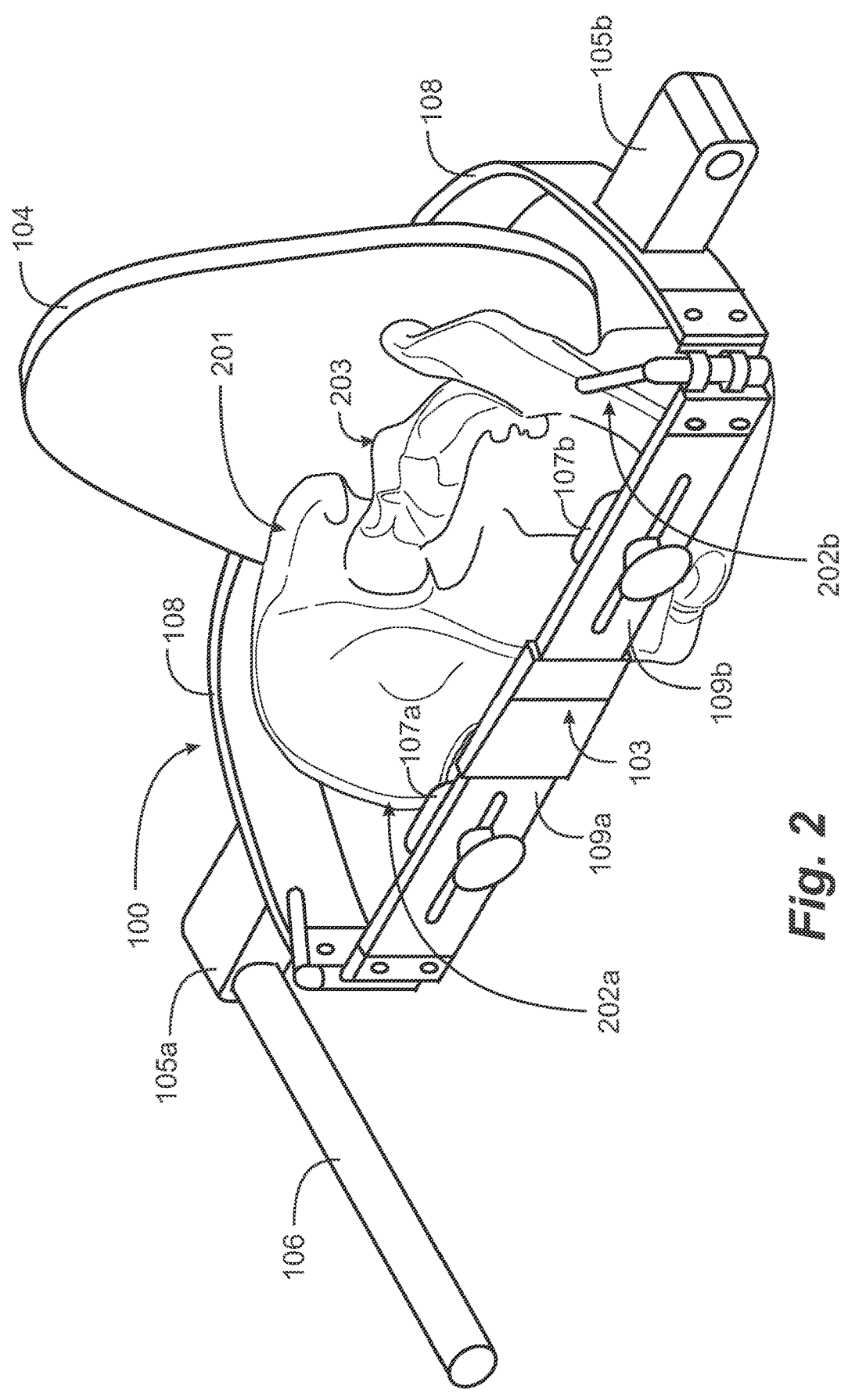
FIG. 2 is a perspective view of the device of FIGS. 1A, 1B, 1C and 1D shown surrounding a patient's hip structure.

FIG. 2 is a perspective view of the device of FIGS. 1A, 1B, 1C and 1D placed around a patient with buckle 103 secured. An outline 201 of the patient's hip-bone structure is illustrated within the surrounding hip flexion medical device of the invention. The ASIS points 202a and 202b on the left and right iliac portions of the pelvis structure are indicated and the PSIS point 203 on the rear of the sacrum is indicated as well. These three points are contact points for the hip flexion medical device in embodiments of the invention. In FIG. 2 the ASIS pads 107a and 107b are shown aligned with the patient's ASIS points, and the PSIS pad 104 is positioned to contact the patient's PSIS point. As the device is tightened on the patient, the respective pads impinge upon the ASIS and PSIS points and manipulating lever 106 provides flexure to the hip structure.

Figure 3:
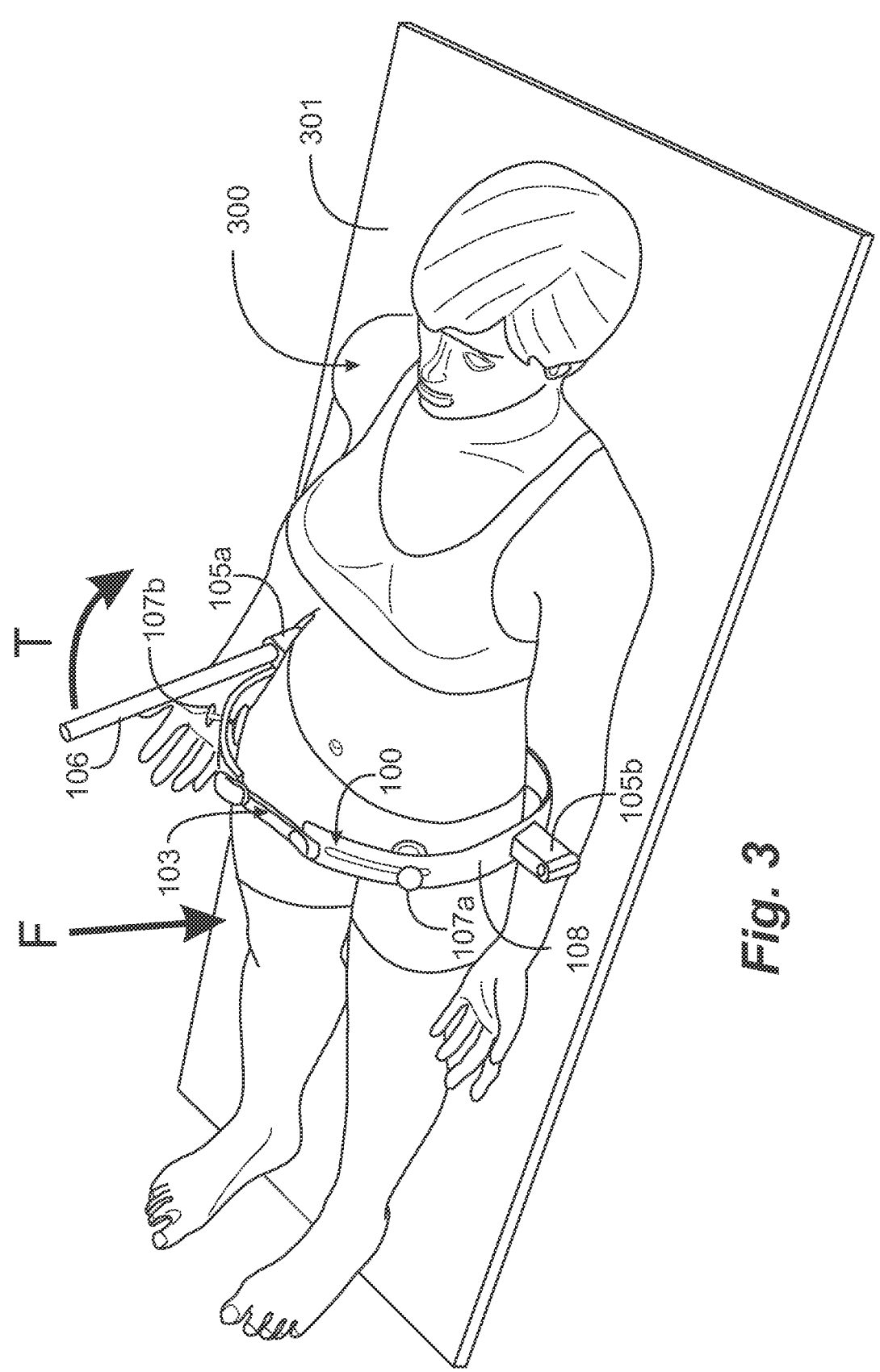
FIG. 3 is a perspective view of a patient on a table for treatment wearing the hip flexion medical device.

FIG. 3 is a perspective view of a patient 300 on a table 301 wearing a hip flexion device 100 according to an embodiment of the present invention. It may be seen that pads 107a and 107b impinge on the ASIS points of the patient with the device secured with ratchet buckle 103. Pad 104 is in back of the patient impinging on the PSIS point. Lever arm 106 enables a physical therapist (not shown) to anchor the hip area on either side of the hip (Force F) and to grasp lever 106 and apply torque T to manipulate the patient's hip structure and stretch the iliopsoas muscle. Much less effort is required of the physical therapist to achieve the required stretch than in a merely manual manipulation.

FIG. 4 is a flow diagram depicting a process by which a therapist may use the device according to an embodiment of the invention to treat a patient. At step 401 the therapist opens ratchet buckle 103 all the way and unlocks the hinges if hinges are used. At step 402 the device is placed around the patient's hip structure. At step 403 the therapist closes the hinges, if used, and adjusts the ratchet buckle until the waistband is secure on the patient. At step 404 the therapist loosens the ASIS pads and adjusts the ASIS pads to the patient's ASIS points. At step 405 the hinges are locked if used. At step 406 the ratchet buckle is closed and tightened. At step 407 the lever arm is engaged in one of the socket posts. And at step 408 the therapist holds the patient down and applies pressure by moving the lever arm repeatedly, flexing the patient's hip structure.

It will be apparent to the skilled artisan that there may be some flexibility in the order of the steps, and after the treatment the hip flexion device of the invention may be removed from the patient.

The skilled artisan will understand that the apparatus and the methods described above are strictly exemplary, and not limiting to the scope of the invention, as there are alternative ways within the scope of the invention that the apparatus might be implemented to perform the necessary functions.

The invention claimed is:

1. A therapeutic medical device comprising:
a waistband having a width and opposite ends;
first and second complementary portions of a ratchet buckle joined to the opposite ends of the waistband, enabling the waistband to be opened and closed, and to be adjusted in overall circumference;
a posterior superior iliac spine (PSIS) pad joined to an inside surface of the waistband at a position, with the ratchet buckle closed, opposite the ratchet buckle;
a first anterior superior iliac spine (ASIS) pad joined through a slot to the inside surface of the waistband joined to a first side of the ratchet buckle, in a manner that the first ASIS pad is adjusted along the slot and secured to the waistband by a first locking mechanism outside the waistband;
a second ASIS pad joined through a slot to the inside surface of the waistband joined to a second side of the ratchet buckle, in a manner that the second ASIS pad is adjusted along the slot and secured to the waistband by a second locking mechanism outside the waistband;
a first socket post having a height less than the width of the waistband secured to the waistband through the height of the first socket post at a point on the waistband; and
a lever arm engaged in a socket in the socket post, the lever arm extending parallel to a plane formed on the waistband.

2. The therapeutic medical device of claim 1, further comprising a second socket post having a height less than the width of the waistband secured to the waistband through the height of the socket post at a position on the waistband directly opposite the first socket post.

3. The therapeutic medical device of claim 1 wherein each ASIS pad has a threaded post extending through the slot and a locking knob engaging the threaded post outside the waistband.

4. A therapeutic medical device, comprising:
a waistband having a width and opposite ends;
a first locking hinge joined to the waistband at one of the opposite ends, and a second locking hinge joined to the waistband at the other opposite end;
a first panel having a first linear slot joined to the first locking hinge and ending at a first portion of a ratchet buckle;
a second panel having a second linear slot joined to the second locking hinge and ending in a second portion of the ratchet buckle;
a posterior superior iliac spine (PSIS) pad joined to an inside surface of the waistband at a position, with the ratchet buckle closed, opposite the ratchet buckle;
a first anterior superior iliac spine (ASIS) pad joined to the first linear slot in the first panel; and
a second ASIS pad joined to the second linear slot in the second panel;
a first socket post having a height less than the width of the waistband secured to the waistband through the height of the socket post at a point on the waistband about ninety degrees from the ratchet buckle; and
a lever arm engaged in a socket in the socket post, the lever arm extending parallel to a plane formed on the waistband.

5. The therapeutic medical device of claim 4, further comprising a second socket post having a height less than the width of the waistband secured to the waistband through the height of the second socket post at a position on the waistband directly opposite the first socket post.

6. The therapeutic medical device of claim 4 wherein each ASIS pad has a threaded post extending through the slot and a locking knob engaging the threaded post outside the waistband.

7. A method for treating s patient for hip flexion contracture, comprising:
placing a therapeutic medical device having a waistband having a width and opposite ends, first and second complementary portions of a ratchet buckle joined to the opposite ends of the waistband, enabling the waistband to be opened and closed, and to be adjusted in overall circumference, a posterior superior iliac spine (PSIS) pad joined to an inside surface of the waistband at a position, with the ratchet buckle closed, opposite the ratchet buckle, a first anterior superior iliac spine (ASIS) pad joined through a slot to the inside surface of the waistband joined to a first side of the ratchet buckle, in a manner that the first ASIS pad is adjusted along the slot and secured to the waistband by a first locking mechanism outside the waistband, a second ASIS pad joined through a slot to the inside surface of the waistband joined to a second side of the ratchet buckle, in a manner that the second ASIS pad is adjusted along the slot and secured to the waistband by a second locking mechanism outside the waistband, a first socket post having a height less than the width of the waistband secured to the waistband through the height of the socket post, and a first lever arm engaged in a socket in the socket post, the first lever arm extending parallel to a plane formed on the waistband, around a hip structure of a patient;

adjusting circumference of the therapeutic medical device and securing the device firmly to the patient;

positioning the first ASIS pad to the patient's first ASIS point and the second ASIS pad to the patient's second ASIS point;

holding the patient securely facing up against a supporting surface; and manipulating the first lever arm, rotating the patient's hip structure and stretching the patient's first iliopsoas muscle.

8. The method of claim 7 further comprising securing a second socket post having a height less than the width of the waistband to the waistband through the height of the second socket post at a point on the waistband opposite the first socket post, engaging a second lever arm in a socket of the second socket post, and manipulating the second lever arm, rotating the patient's hip structure and stretching the patient's second iliopsoas muscle.

8

* * * * *